United States Patent
Garvin et al.

(10) Patent No.: US 9,561,261 B2
(45) Date of Patent: Feb. 7, 2017

(54) RELAXIN PROTEINS FOR USE IN THE DIAGNOSIS, PREVENTION OR TREATMENT OF MULTIPLE SCLEROSIS

(75) Inventors: Roy Garvin, Central Point, OR (US); Alasdair Burns, Central Point, OR (US)

(73) Assignee: BVBIOMED LTD., Glasgow (GB)

( * ) Notice: Subject to any disclaimer, the term of this patent is extended or adjusted under 35 U.S.C. 154(b) by 187 days.

(21) Appl. No.: 14/128,919

(22) PCT Filed: Jun. 25, 2012

(86) PCT No.: PCT/EP2012/062255
§ 371 (c)(1),
(2), (4) Date: Apr. 25, 2014

(87) PCT Pub. No.: WO2012/175744
PCT Pub. Date: Dec. 27, 2012

(65) Prior Publication Data
US 2014/0256633 A1    Sep. 11, 2014

(30) Foreign Application Priority Data

Jun. 24, 2011 (GB) .................................. 1110833.9

(51) Int. Cl.
*A61K 38/22* (2006.01)
*C12Q 1/68* (2006.01)
*G01N 33/74* (2006.01)

(52) U.S. Cl.
CPC ......... *A61K 38/2221* (2013.01); *C12Q 1/6883* (2013.01); *G01N 33/74* (2013.01)

(58) Field of Classification Search
None
See application file for complete search history.

(56) References Cited

U.S. PATENT DOCUMENTS

| | | | |
|---|---|---|---|
| 4,683,202 A | 7/1987 | Mullis | |
| 2005/0026822 A1* | 2/2005 | Tregear | C07K 14/64 514/4.7 |
| 2006/0052304 A1* | 3/2006 | Stewart | A61K 38/2221 514/11.3 |
| 2009/0311185 A1* | 12/2009 | Hida | A61K 38/2221 424/9.2 |
| 2011/0243942 A1* | 10/2011 | Wang | C07K 14/64 424/134.1 |

FOREIGN PATENT DOCUMENTS

| | | |
|---|---|---|
| EP | 1880728 | 1/2008 |
| WO | WO 2010/140060 A2 | 12/2010 |
| WO | WO 2012/175744 | 12/2012 |

OTHER PUBLICATIONS

Van Der Westhuizen, et al; "Relaxin Family Peptide Receptors—From Orphans to Therapeutic Targets"; Drug Discovery Today, vol. 13, Nos. 15/16; Aug. 2008.
Altschul et al. J. Mol. Biol. vol. 215, 1990, pp. 403-410.
Altschul et al. Nuc Acids Res. vol. 25, 1997, pp. 3389-3402.
Devereux J et al. Nucl Acid Res vol. 12, 1984, pp. 387-395.
Eckert et al. PCR Methods and Applications vol. 1, 1991, pp. 17-24.
Guatelli et al. Proc Natl Acad Sci USA vol. 87 (5), 1990, pp. 1874-1878.
Henikoff S.; Henikoff JG, Proc. Nat. Acad. Sci.; USA vol. 89 (22), 1992, pp. 10915-10919.
Kwoh et al. Proc Natl Acad Sci USA vol. 86 (4), 1989, p. 1173-1177.
Landegren. et al. Science vol. 241, 1988, p. 1077-1080.
Mattila et al. Nucleic Acids Res. vol. 19 (18), 1991, p. 4967-4973.
Neddleman; Wunsch J. Mol. Biol. vol. 48 (3), 1970, pp. 443-453.
Pearson W.R.; Lipman D.J. Proc. Nat. Acac. Sci., USA vol. 85 (8), 1988, pp. 2444-2448.
Tyle, P. Pharmaceutical Research vol. 3, No. 6, 1986, pp. 318-326.
Smith; Waterman Advances in Applied Mathematics vol. 2, 1981, pp. 482-489.
Sudo et al. J.Biol.Chem vol. 278, No. 10, Mar. 7, 2003, pp. 7855-7862 (also published online, JBC Papers in Press, Dec. 27, 2002; which online publication may or may not differ from final printed publication).
Wu et al. Genomics vol. 4, 1989, p. 560-569.
International Search Report for International Application No. PCT/EP2012/062255, mailed Oct. 16, 2012.
Garvin et al., "A pilot study of relaxin in multiple sclerosis: diagnostic and therapeutic implications", (Oct. 2011), Abstract from the 5th Joint Triennial Congress of the European and Americas Committees for Treatment and Research in Multiple Sclerosis, Amsterdam, The Netherlands (Oct. 19, 2011-Oct. 22, 2011), Retrieved from the Internet, URL:http://registration.akm.ch/einsicht.php?XNABSTRACT_ID=139444&XNSPRACHE_ID=2&XNKONGRESS_ID=150&XNMASKEN_ID=900 (Date Accessed: Mar. 16, 2016).

* cited by examiner

*Primary Examiner* — David Romeo
(74) *Attorney, Agent, or Firm* — Hoxie & Associates LLC

(57) ABSTRACT

The present invention relates to the use of one or more Relaxin proteins in methods for diagnoses and treatment of multiple sclerosis. The invention also provides compositions for use in diagnosing or treating multiple sclerosis as well as the methods themselves. Kits for carrying out the methods are also described.

6 Claims, 6 Drawing Sheets b a

RELAXIN PROTEINS FOR USE IN THE DIAGNOSIS, PREVENTION OR TREATMENT OF MULTIPLE SCLEROSIS

CROSS REFERENCE TO RELATED APPLICATIONS

This application is a United States National Stage Application under 35 U.S.C. 371 of PCT Application No. PCT/EP2012/062255, filed on Jun. 25, 2012, which claims the benefit of GB 1110833.9, filed Jun. 24, 2011.

The present invention relates to the use of one or more Relaxin proteins in methods for diagnoses and treatment of multiple sclerosis. The invention also provides compositions for use in diagnosing or treating multiple sclerosis as well as the methods themselves.

Multiple sclerosis (MS), an inflammatory demyelinating disease of the central nervous system (CNS), is a major cause of disability in young adults. In most patients the disease ultimately has a progressive course which manifests itself during or after a preceding phase of relapses and remissions (secondary progressive (SP) disease). In a small percentage of patients (10-15%) the disease course is progressive from onset (primary progressive (PP) disease) without the relapsing phases of the disease. The currently available treatments for multiple sclerosis are aimed at suppressing the autoimmune component of the disease and/or down regulating the inflammation. To date, the main clinical impact of these therapies is on the number and severity of relapses. The effect on permanent disability is much less well established.

MS is initially characterized by plaques in the brain which are seen on MRI and are attributed to areas of inflammation and areas of demyelination. Repeated cycles of inflammation in the same area of the brain contribute to demyelination. The demyelination of the nerve fibers of the brain and spinal cord then results in chronic lesions on the brain. These areas of inflammation and demyelination cause multiple and varied neurologic symptoms and signs, usually with relapses and remissions. Frequently, a diagnosis of MS may not be made for many years after the onset of symptoms. This is because there is no definitive test for MS. A clinically based diagnosis is difficult because the symptoms are so variable and sporadic and can be similar to those of other disorders.

The clinical course of MS is also highly variable and unpredictable, with patients experiencing acute relapses followed by periods of remission. Early in the disease they experience fatigue and tremors and become increasingly less ambulatory. Although the disease progression varies among patients, it almost always proceeds to a chronic, degenerative state. And as the disease progresses they lose the use of the lower extremities becoming paraplegic. As their nervous system becomes more affected, the later stages of the disease are characterized by total paralysis and/or death.

MS may occur in several forms classified as primary progressive, relapsing-remitting, and secondary progressive, depending on the pathophysiology, progression and severity of the symptoms. The physiological differences between these forms of the disease are not fully understood. There are several theories as to the causes of MS, however, the precise causes of the disease have not yet been established. Research to date has indicated that the onset of MS is at least in part due to genetic factors, whereas progression of the disease may be influenced by both genetics and other external factors.

A definitive diagnosis of MS usually occurs between the ages of 25 and 35. However, clinical studies have indicated that initial symptoms of the disease occur in the late teens and that there is a sex bias of 2 to 1, female to male. It has also been well established that in female patients the symptoms of MS go into remission during pregnancy and worsen during menstruation. These findings suggest a possible role for growth and sex hormones in the onset and progression of the disease.

Sex related differences in the course and severity of multiple sclerosis (MS) have been noted before. These differences are thought to be caused by different profiles of sex hormones in women and men. During pregnancy the symptoms of MS go into remission through the third trimester. MRI studies have shown that brain lesion activity is modulated by the levels of the sex hormones testosterone and estrogen. During pregnancy the estrogens; estradiol (E2) and estriol (E3) rise during the second and third trimesters and modulate disease activity in MS. Initial studies have shown E2 and E3 to be useful candidates for the treatment of exacerbations in MS. A large Phase 2 clinical trial is currently underway to assess the efficacy of estrogens as a treatment for women with MS.

In men with MS the sex hormone testosterone has been shown to help alleviate some of the symptoms. As with estrogen, clinical trials are currently underway to assess testosterone as a treatment for MS in men.

Both testosterone and estrogen reduce MS symptoms by modulating matrix metalloproteinases (MMP), interleukins (IL) and protein kinase C (PKC). Both testosterone and estrogen act through the relaxin (RLX) pathway. Testosterone and estrogen stimulation of the sex hormone RLX2 regulates MMP, IL and PKC.

RLX2 is a member of the relaxin family of peptides comprising RLX1, RLX2 and RLX3. RLX1 and RLX2 are both circulating proteins which bind the same receptors to down regulate inflammation, modulate autoimmunity, and assist in neuronal function and vasodilatation. They differ in their regulation: RLX1 is present at all times in the body and up regulated by stress and the inflammatory response, RLX2 production is up regulated by estradiol and growth hormones. Unlike RLX1 and RLX2, RLX3 has been classified as a neurotransmitter which is produced in the brain. It primarily binds the G protein coupled receptors (GPCR) 135 and 142. Through binding these GPCR's RLX3 plays an important role sensory processing and modulating localized inflammation.

RLX1 and RLX2 are pleiotropic proteins which influence multiple pathways (FIG. 6). RLX1 and RLX2 bind the relaxin family protein receptor 1 (RXFP 1), the glucocorticoid receptor (GR), the endothelin type-B receptor ($ET_B$) and the estrogen receptor β (ERIβ).

Of special interest is the binding of RLX to RXFP1. RXFP1 was previously named the orphaned G-protein coupled receptor 7. Studies have indicated that elevated levels of GPCR's may have important consequences for the onset and progression of MS. As agonists of RXFP1/GPCR7, maintaining the proper level of RLX1 and/or RLX2 could be important in regulating expression of RXFP 1.

Another GPCR (GPCR17) which has been implicated in the development of MS symptoms. In a mouse model with over expression of GCPR17 the animals developed the symptoms of EAE, namely, they experienced fatigue, tremors and loss of function in the hind limbs leading to death, mimicking the symptoms and disease course associated with MS. RLX strongly up regulates the level of progesterone which causes a marked decrease in expression of GPCR17.

Binding of RLX1 and RLX2 to their receptor array results in the modulation of the $ET_B$, ER, GCR and RXFP1 receptor pathways (FIG. 6). Through $ET_B$ RLX1 increases NF-dB and decreases endothelin-1 levels which leads to vasodilation. Recent studies suggest that a decrease in cerebral blood flow may play a role in the etiology of MS. RLX binding to ER β1 and β2 and down regulates the production of cyclooxygenase-2 (COX-2) which may play a role in the disease. Binding of RLX1 to its feedback receptor GCR down regulates inflammation and modulates RLX1 production via a feedback loop. GCR binding has also been shown to stimulate the production of ACTH. Studies have shown ACTH to be an effective treatment for acute exacerbations in MS.

The binding of RLX to RXFP 1 is of particular interest as RXFP1 stimulation also increases the level of ACTH. In addition, it elevates the levels of TK and PKC which are important in maintaining the integrity of the BBB. Of particular interest is the role of RXFP1 as an agonist of PPAR-γ. It is likely that the protective effects of RXFP1 agonists in EAE previously reported are in fact due to the downstream effect of RXFP1 activation on PPAR-γ. Research into the use of the PPAR-γ agonist pioglitazone has been shown to be effective in preventing EAE and in altering the course and progression of MS. A clinical trial using pioglitazone in MS showed that it was effective in preventing exacerbations and modifying the course of the disease; serial MRI showed no new lesions or lesion activity while on treatment.

RLX 3 has been shown to bind strongly to GPR8 and weakly to GPR7 which up-regulates the expression of GCPR 135. GCPR 135 is of interest in MS as it is also known as somatostatin. Levels of somatostatin have been shown to be decreased in patients with MS. It is also known to regulate levels of the phospholipid transfer protein (PLTP). PLTP transfer activity is increased in patients with MS. However cellular uptake of lipids through PLTP has been shown to be decreased in MS, indicating a problem with the PLTP/APO A1 uptake mechanism.

We describe herein genetic defects in RLX 1 and RLX 3 which are present in subjects with MS. The genetic defects identified in the gene encoding RLX 1 consist of 19 SNP's located within exon 1 (see table 4). These mutations cause changes in the DNA sequence (see table 1, comparing SEQ ID NO: 1 to SEQ ID NO: 2) and the protein sequence (see table 2, comparing SEQ ID NO: 3 to SEQ ID NO: 4).

The variations in the sequence of RLX1 found in subjects with MS could have an effect of the β chain binding cassette region. The β chain binding cassette has been shown to be controlled by both its geometry and electrostatic forces. Protein modeling was performed to determine the effect of amino acids substitutions on the structure and function of the binding site using Swiss Prot. Changes in the Protein's geometry were observed between the wild type and MS. (See FIG. 1). The electrostatic forces associated with the binding site were also greatly altered (See FIG. 2).

The result of a decrease in the function of RLX 1 would be an increase in inflammation and an up-regulation of GCPR 17. Over expression of GCPR 17 would cause the symptoms of fatigue, tremors and loss of function in the limbs. These coupled with an increase in the inflammation are the clinical signs and symptoms of MS. In addition, since RLX2 binds the same ligands as RLX 1 (GCPR 17) this would explain the absence of these signs and symptoms during periods of growth and pregnancy in subjects with MS.

The gene for RLX 3 contains an SNP within the promoter region. This SNP may affect the expression of RLX 3. Down-regulation of RLX 3 would cause a decrease in GCPR 135/somatostatin and abnormal PLTP levels. These have both been shown to exist in subjects with MS.

These SNP's can form the basis of diagnostic tests and treatments for the disease.

Previous studies using plasma infusions have demonstrated that the plasma fraction, which of course contains the RLX's from normal subjects is able to clinically reverse exacerbations in as little as 24 hours. However, for the first time we are able to explain this result. Therefore RLX 1, RLX2 or RLX 3 could all be used as the basis of a treatment for the clinical symptoms of the disease. With their varying ability to bind the LRG7 receptor and down-regulate inflammation, they may also be useful in treating the sub-clinical symptoms, slowing or halting the onset and progression of clinical disease.

Thus, in a first aspect, the present invention provides one or more Relaxin proteins (RLXs) for use in the prevention or treatment of Multiple Sclerosis (MS). The RLXs which are particularly useful in the present invention include RLX1, RLX2 and RLX3, as well as variants and homologues of those proteins. Variants or homologues in the context of the present invention is intended to encompass proteins which are functionally equivalent to RLX1, RLX2 and RLX3, but which have sequences which vary from the native ones. Such variants or homologues will also include functional fragments of the complete protein. Particularly preferred homologues include Prorelaxins and Preprorelaxins. As used herein "prorelaxin" refers to the prohormone form of relaxin which contains an additional peptide chain as compared to the heterodimer relaxin protein. "Preprorelaxin" refers to a precursor of prorelaxin which contains a secretory signal.

The skilled person will appreciate that homologues or variants of the proteins or polypeptides of the invention will also find use in the context of the present invention, ie able to bind to the relaxin receptor. Thus, for instance proteins or polypeptides which include one or more additions, deletions, substitutions or the like are encompassed by the present invention. In addition, it may be possible to replace one amino acid with another of similar "type". For instance replacing one hydrophobic amino acid with another.

One can use a program such as the CLUSTAL™ program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment.

"% identity" is a measure of the relationship between two nucleic acid or polypeptide sequences, as determined by comparing their sequences. In general, the two sequences to be compared are aligned to give a maximum correlation between the sequences. The alignment of the two sequences is examined and the number of positions giving an exact amino acid or nucleotide correspondence is determined, and divided by the total length of the alignment, and the result is multiplied by 100 to give a % identity. The % identity may be determined over the whole length of the sequence to be compared, which is particularly suitable for sequences of the same or similar lengths or for sequences which are highly homologous, or over shorter defined lengths which is more suitable for sequences of unequal lengths and with a lower homology.

Methods for comparing the identity of two or more sequences are known in the art. For example, programs available in the Wisconsin Sequence Analysis Package version 9.1 (Devereux J et al., *Nucl Acid Res* 12 387-395

(1984), available from Genetics Computer Group, Madison, Wis., USA), such as BESTFIT and GAP may be used.

BESTFIT uses the "local homology" algorithm of Smith and Waterman (Advances in Applied Mathematics, 2:482-489, 1981) and finds the best single region of similarity between two sequences. BESTFIT is more suited to comparing two polynucleotide or two polypeptide sequences which are dissimilar in length, the program assuming that the shorter sequence represents a portion of the longer. In comparison, GAP aligns two sequences finding a "maximum similarity" according to the algorithm of Neddleman and Wunsch (J. Mol. Biol. 48:443-354, 1970). GAP is more suited to comparing sequences which are approximately the same length and an alignment is expected over the entire length. Preferably, the parameters "Gap Weight" and "Length Weight" used in each program are 50 and 3 for polynucleotide sequences and 12 and 4 for polypeptide sequences, respectively. Preferably, % identities and similarities are determined when the two sequences being compared are optimally aligned.

Other programs for determining identity and/or similarity between sequences are also known in the art, for instance the BLAST family of programs (Altschul et al, *J Mol. Biol.,* 215:403-410, (1990) and Altschul et al, *Nuc Acids Res.,* 25:289-3402 (1997), available from the National Center for Biotechnology Information (NCB), Bethesda, Md., USA and accessible through the home page of the NCBI at www.ncbi.nlm.nih.gov) and FASTA (Pearson W. R. and Lipman D. J., *Proc. Nat. Acac. Sci., USA,* 85:2444-2448 (1988), available as part of the Wisconsin Sequence Analysis Package). Preferably, the BLOSUM62 amino acid substitution matrix (Henikoff S. and Henikoff J. G., *Proc. Nat. Acad. Sci., USA,* 89:10915-10919, (1992)) is used in polypeptide sequence comparisons including where nucleotide sequences are first translated into amino acid sequences before comparison.

Preferably, the program BESTFIT is used to determine the % identity of a query polynucleotide or a polypeptide sequence with respect to a polynucleotide or a polypeptide sequence of the present invention, the query and the reference sequence being optimally aligned and the parameters of the program set at the default value.

In the case of homologues and variants, the degree of identity with a protein or polypeptide as described herein is less important than that the homologue or variant should retain the functionality of the original protein or polypeptide. However, suitably, homologues or variants having at least 60% similarity (as discussed above) with the proteins or polypeptides described herein are provided. Preferably, homologues or variants having at least 70% similarity, more preferably at least 80% similarity are provided. Most preferably, homologues or variants having at least 90% or even 95% similarity are provided.

For fragments of the proteins or polypeptides described herein, or of homologues or variants thereof, the situation is slightly different. It is well known that is possible to screen a protein or polypeptide to identify the binding regions, ie those regions which are responsible for the protein or polypeptide's functionality. Methods for carrying out such screening are well known in the art. Thus, the fragments of the present invention should include one or more such binding regions or be sufficiently similar to such regions to retain their functional properties. Thus, for fragments according to the present invention the degree of identity is perhaps irrelevant, since they may be 100% identical to a particular part of a protein or polypeptide, homologue or variant as described herein. The key issue, once again, is that the fragment retains the functional properties. In the present application, fragments are any contiguous 10 amino acid sequence, or greater, such as 20, 30, 40, or 50 amino acid sequence.

Naturally occurring biologically active relaxin may be derived from human, murine (ie rat or mouse), porcine or other mammalian sources. The term "Relaxin" encompasses human H1 preprorelaxin, prorelaxin and relaxin; H2 preprorelaxin, prorelaxin and relaxin; recombinant human relaxin (rhRLX); and H3 preprorelaxin, prorelaxin and relaxin. H3 relaxin has been described in the art (see for example Sudo et al (2003) *J. Biol. Chem* 7; 278(10):7855-62). The Relaxin proteins of the present invention can be obtained from any known source, including isolation from human or animal plasma, as well as human or animal organs. For instance, a form of porcine pituitary Relaxin could be used. However, it is usually more convenient to produce the proteins recombinantly. Such methods for producing the proteins are well known to those skilled in the art.

The amino acid sequences of human relaxin are described in the art. For example, human relaxin amino acid sequences are found under the following Gen Bank Accession Nos.: Q3WXF3, human H3 prorelaxin; P04808, human H1 prorelaxin; NP_604390 and NP_005050, human H2 prorelaxin; AAH05956, human relaxin 1 preproprotein; NP_008842, human H1 preprorelaxin; etc.

As already described herein, the Relaxins are useful in treating Multiple Sclerosis. Thus, in a second aspect, the present invention provides a pharmaceutical composition for use in the treatment of Multiple Sclerosis, which comprises one or more Relaxins, preferably one or more of Relaxin 1, Relaxin 2 and Relaxin 3, optionally together with one or more pharmaceutically acceptable carriers, excipients or diluents. Preferably the one or more relaxins is a variant or homologue or fragment of the native protein.

The compositions of the invention may be presented in unit dose forms containing a predetermined amount of each active ingredient per dose. Such a unit may be adapted to provide 5-100 mg/day of the compound, preferably either 5-15 mg/day, 10-30 mg/day, 25-50 mg/day 40-80 mg/day or 60-100 mg/day. For compounds of formula I, doses in the range 100-1000 mg/day are provided, preferably either 100-400 mg/day, 300-600 mg/day or 500-1000 mg/day. Such doses can be provided in a single dose or as a number of discrete doses. The ultimate dose will of course depend on the route of administration and the age, weight and condition of the patient and will be at the doctor's discretion.

The compositions of the invention may be adapted for administration by any appropriate route, for example by the oral (including buccal or sublingual), nasal, topical (including buccal, sublingual or transdermal) or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists which may be generated by means of various types of metered dose pressurised aerosols, nebulizers or insufflators.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Preferred unit dosage formulations are those containing a daily dose or sub-dose, as herein above recited, or an appropriate fraction thereof, of an active ingredient.

It should be understood that in addition to the ingredients particularly mentioned above, the formulations may also include other agents conventional in the art having regard to the type of formulation in question, for example those suitable for oral administration may include flavouring agents.

In a further aspect, the present invention provides a method of treating Multiple Sclerosis which comprises administering to a subject one or more Relaxins, preferably one or more of Relaxin 1, Relaxin 2 and Relaxin 3 or a variant or homologue thereof. In addition, as already described herein, we have shown that patients suffering from Multiple Sclerosis have particular mutations in the sequence of their Relaxin proteins. This finding enables diagnosis of Multiple Sclerosis, even before observable onset of the disease and indeed allows early recognition of a predisposition to Multiple Sclerosis.

Thus, in yet a further aspect, the present invention provides a method for diagnosis of Multiple Sclerosis, which comprises the step of identifying whether a subject has one or more mutant Relaxin proteins. In the context of the present invention "mutant" indicates a non wild type protein. This can conveniently be achieved by comparing one or more Relaxin proteins from a subject with native or wild type equivalent. Preferably, one or both of Relaxin 1 or Relaxin 3 are compared.

Methods for comparing sequences are well known to the person skilled in the art. For example nucleic acids can be obtained from a sample such as blood sample, and the relaxin gene sequenced. The resulting sequences can then be compared using software such as described above for calculating percentage identity.

The diagnostic methods can be carried out on a sample removed from the subject's body. The sample can be derived from any biological sample which contains the subject's nucleic acid or protein. For example, the biological sample can be a sample of whole blood, plasma, serum, urine, sputum or lymph and can be obtained by any suitable means.

The above described methods may require amplification of the DNA sample from the subject, and this can be done by techniques known in the art, such as PCR (see *PCR Technology: Principles and Applications for DNA Amplification* (ed. H. A. Erlich, Freeman Press, NY 1992; *PCR Protocols: A Guide to methods and Applications* (eds. Innis et al., Academic press, San Diego, Calif. 1990); Mattila et al., *Nucleic Acids Res.* 19 4967 (1991); Eckert et al., *PCR Methods and Applications* 117 (1991) and U.S. Pat. No. 4,683,202. Other suitable amplification methods include ligase chain reaction (LCR) (Wu el al., *Genomics* 4 560 (1989); Landegran et al., *Science* 241 1077 (1988)), transcription amplification (Kwoh et al., *Proc Natl Acad Sci USA* 86 1173 (1989)), self sustained sequence replication (Guatelli et al., *Proc Natl Acad Sci USA* 87 1874 (1990)) and nucleic acid based sequence amplification (NASBA). The latter two methods both involve isothermal reactions based on isothermal transcription which produce both single stranded RNA and double stranded DNA as the amplification products, in a ratio of 30 or 100 to 1, respectively.

Methods for identifying the presence of mutant proteins are also known to the skilled person. For example it is known that mutant forms of the relaxin protein can have altered binding to the receptors. Changes in the ability of the protein to bind to the receptor can be assessed using standard techniques such as ELISA, Western blots, competitive binding assays etc.

In a preferred embodiment the Relaxin protein is Relaxin 1 and the method comprises identifying the presence of one or more single-nucleotide polymorphisms (SNPs). This identification step can comprise either directly sequencing DNA or protein obtained from the subject. Alternatively, the method can comprise identification of a modified protein by means of for example, antibodies raised against "normal" or "mutant" Relaxin.

In another preferred embodiment the protein is Relaxin 3 and comprises the step of identifying an SNP preferably in the promoter region of the gene encoding Relaxin 3. Again, this can be achieved by directly sequencing DNA from a subject. Alternatively, measuring levels of Relaxin 3 in a subject and comparing with a baseline value obtained from "normal" subjects would allow confirmation of altered regulation of Relaxin 3 production.

In another aspect the invention provides another method for diagnosing MS, which comprises measuring the level of a relaxin protein in a sample obtained from a patient. Abnormal levels of circulating relaxins in the body indicate MS. Preferably the relaxin protein is RLX 1, RLX2 and/or RLX3. The sample is preferably a blood sample. As used herein a blood sample refers to whole blood, plasma or sera sample. Preferably this method is used in conjunction with a genetic screen for the mutations of the relaxin 1 gene.

Protein levels can be measured by a number of available assays and procedures known to the skilled person, such as ELISA and Western blotting. One method used herein utilizes antibodies developed against relaxin to detect protein levels by ELISA. The protein levels measured in the patient samples can be compared to levels obtained from normal healthy controls, who do not have MS, in order to determine whether the levels observed in the patients are elevated. These levels can be used to diagnose MS and to differentiate between relapsing remitting (RR), chronic progressive (CP) and secondary progressive (SP) MS. In subjects with RR and CP MS elevated levels of relaxin are observed. Subjects with SP MS have no measureable levels of relaxin in the sera. This would enable the correct treatment options to be selected.

In a further aspect the present application also provides kits for carrying out the methods of the invention. The methods or kits of the invention may involve the determination of a polymorphism in the RLX1 or RLX3 gene. Such polymorphisms may include SNPs, mutations, insertions, deletions or translocations. Any polymorphisms in the RLX1 or RLX3 gene may affect the expression of the RLX1 or RLX3 protein, and such polymorphisms may therefore be indicative of a subject's risk of developing MS. Thus, the invention provides a method of diagnosing, or determining predisposition or susceptibility of a subject to MS, comprising determining the presence of at least one variant of an RLX1 or RLX3 gene in the subject.

The methods and kits of the invention may comprise the use of primers and probes. Primer sequences are capable of acting as an initiation site for template directed nucleic acid synthesis, under appropriate conditions, which will be known to skilled persons. Probes are useful in the detection, identification and isolation of particular nucleic acid sequences, such as the RLX1 or RLX3 gene sequence. Probes and primers are preferably 15 to 30 nucleotides in length.

For amplification purposes, pairs and primers are provided. These include a 5' primer, which hybridises to the 5' end of the nucleic acid sequence to be amplified, and a 3' primer, which hybridises to the complementary strand of the 3' end of the nucleic acid to be amplified.

Probes and primers may be labelled, for example to enable their detection. Suitable labels include for example, a radiolabel, enzyme label, fluoro-label, and biotin-avidin label for subsequent visualisation in, for example, a southern blot procedure. A labelled probe or primer may be reacted with a sample DNA or RNA, and the areas of the DNA or RNA which carry complementary sequences will hybridise to the probe, and become labelled themselves. The labelled areas may be visualised, for example by autoradiography.

Suitable primers and probes can be designed in order to ensure binding to the RLX1 or RLX3 gene sequence, or a fragment thereof, or a specific polymorphism in the RLX1 or RLX3 gene sequence.

The present invention also provides one or more Relaxin proteins for use in the prevention or treatment of MS by one or more of the following mechanisms:

The elevation of progesterone by relaxin; the decrease in GPCRI7 expression mediated by relaxin; activation of the glucocorticoid receptor to increase interleukin-10, T-helper cells 2, cyclic adenosine triphosphate, adrenocorticotropic hormone and decrease TH-1; binding to the relaxin family receptor RXFP1 to increase ACTH, Tyrosine Kinase, Protein kinase C, the triplex forming oligonucleotide; RXFP1 binding to the peroxisome proliferator-activated receptor gamma which lowers interleukin 12; binding to the endothelin type-B receptor to decrease endothelin-1 levels; binding to the estrogen receptor to increase tyrosine kinase and protein kinase C and to decrease production of cyclooxygenase-2 and the matrix metalloprotease 9.

Preferred features of each aspect of the invention are as for each of the other aspects mutatis mutandis. The prior art documents mentioned herein are incorporated to the fullest extent permitted by law.

The invention will now be described with reference to the following examples, which should not be construed as being in any way limiting. The examples refer to the following figures.

Figure 3:
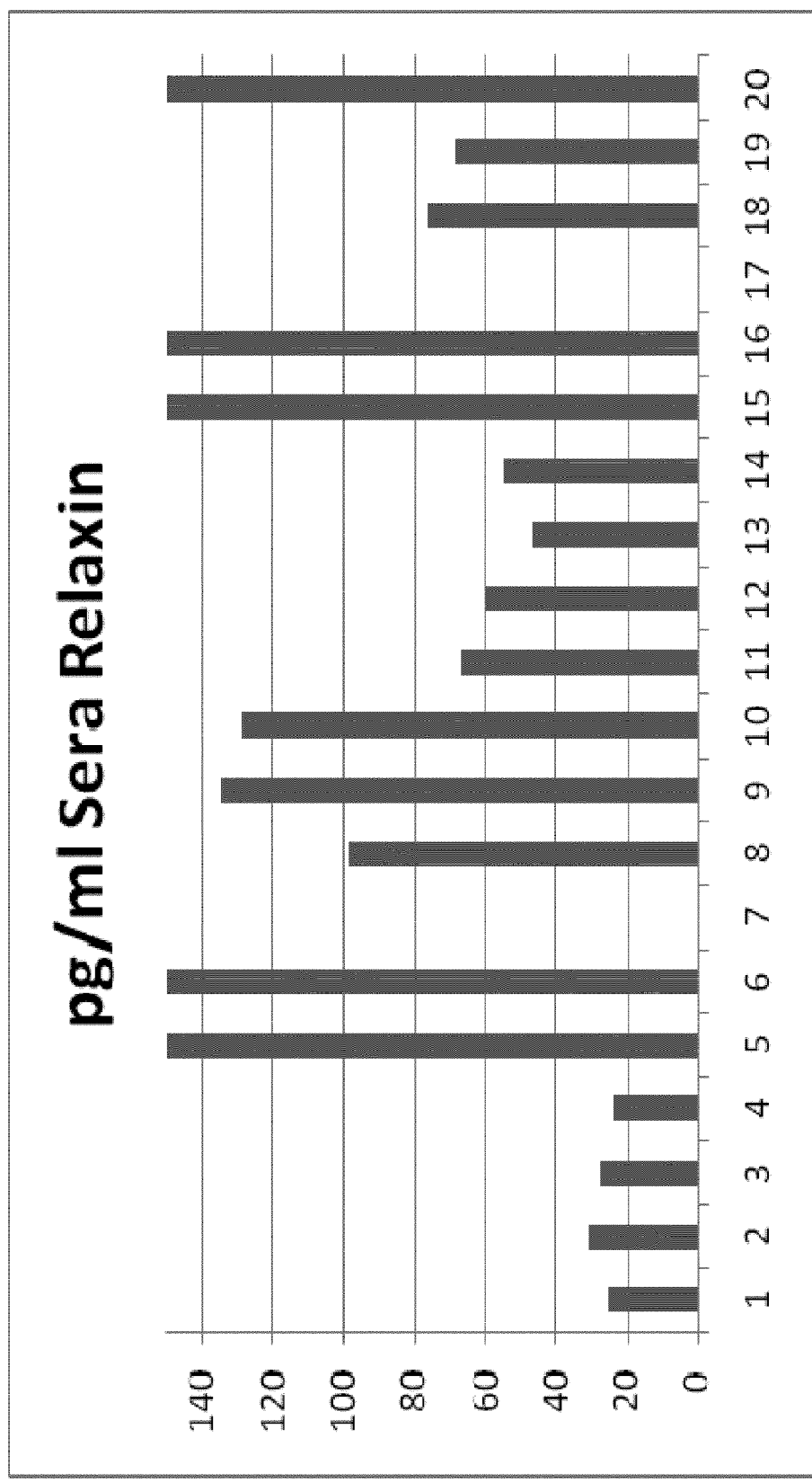

FIG. 3 shows Relaxin levels in MS and controls. Relaxin was elevated in RR and CP MS and undetectable in SPMS samples. This would indicate a distinct difference in etiology between SPMS and other forms of the disease.

Figure 4:
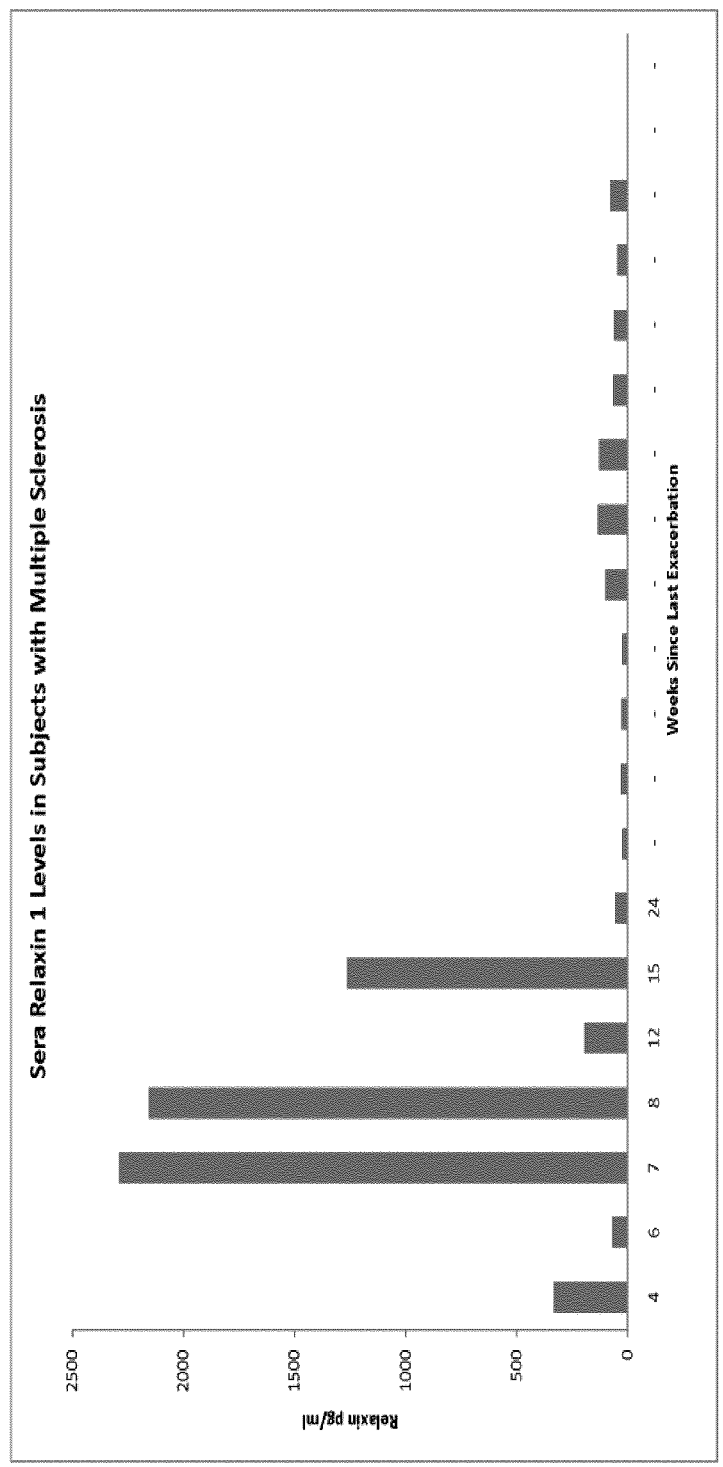

FIG. 4 shows the correlation between relaxin levels and time since the last exacerbation. Levels of RLX1 in both relapsing remitting (RR) and primary progressive (PP) MS were significantly elevated (RR Ave=332.5 pg/ml & PP Ave=76.2 pg/ml). Relaxin levels did not correlate with differences in age or sex, although there was a correlation between relaxin levels and the time since last exacerbation.

Figure 5:
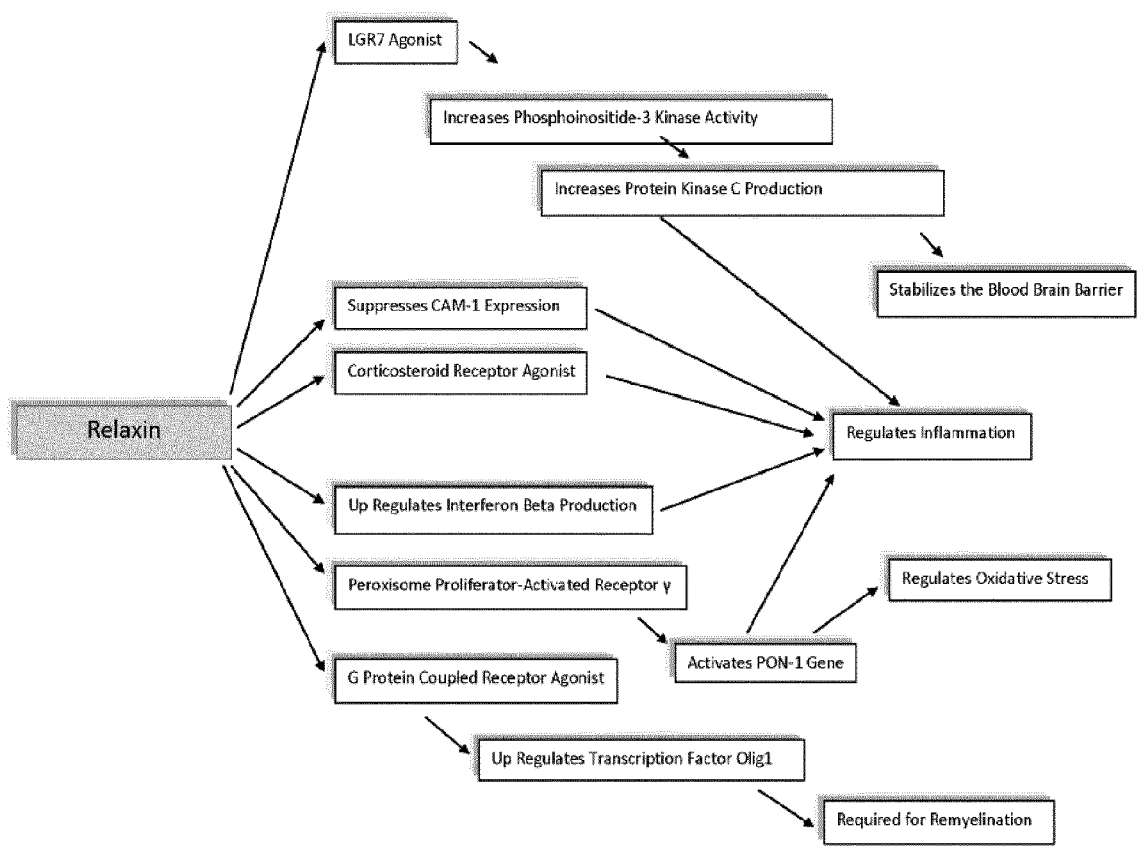

FIG. 5 shows the multiple binding sites and modes of action for Relaxin 1 and Relaxin 2.

Figure 6:
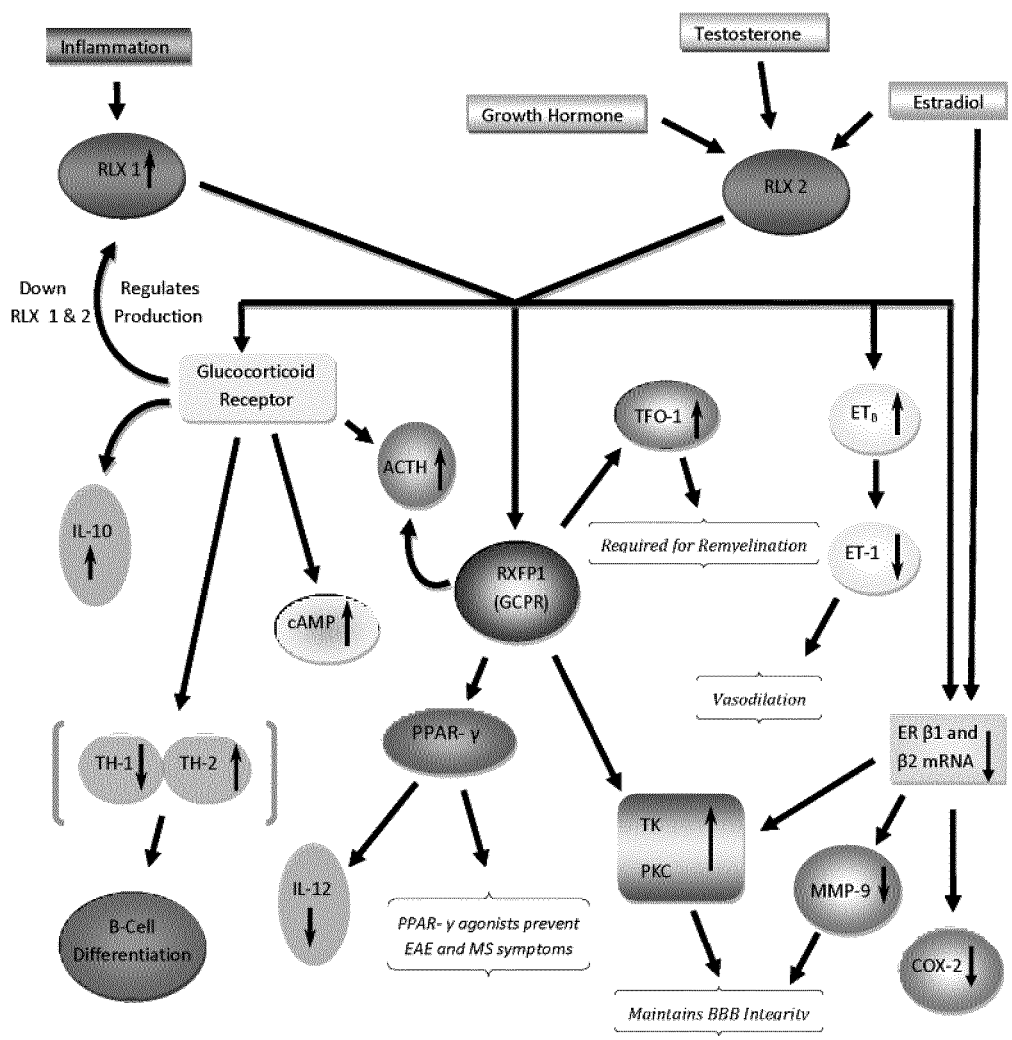

FIG. 6 shows the relaxin activity pathways. Relaxin 1 (RLX1) produced in response to inflammation, relaxin 2 (RLX2) produced by oestradiol, testosterone and growth hormones, act through the same receptors. The glucocorticoid receptor (GCR) increases interleukin-10 (IL-10), T-helper cells 2 (TH-2), cyclic adenosine triphosphate (cAMP), adrenocorticotropic hormone (ACTH) and decreases TH-1. The relaxin family receptor RXFP1 increases ACTH, Tyrosine Kinase (TK), Protein kinase C (PKC) the triplex forming oligonucleotide (TFO-1) and binds the peroxisome proliferator-activated receptor gamma (PPAR-γ) which lowers interleukin 12 (IL-12). The endothelin type-B receptor ($ET_B$) decreases endothelin-1 (ET-1) levels and the Estrogen receptor (ER) increases TK and PKC and decreases production of cyclooxygenase-2 (COX-2), and the matrix metalloprotease 9.

EXAMPLE 1

Identification of Polymorphisms in Relaxin Proteins in MS Patients

We looked at a sample of 24 patients from completely unrelated families with confirmed RR or CP MS. The Relaxin gene from each patient was sequenced and compared with control samples and the published sequences in genebank.

We then confirmed the SNPs by Seqwright Inc. of Texas. Details of the SNPs are shown in Table 4.

TABLE 1

Sequence alignment of control and MS RLX 1

```
GGTTGAGCCGGGTAGGGAAAGCAGCCTAAAGCCCGGGACAGGCACACAGGCCCAGGTGTGTAGGCCACAGCAGCCGCAGTCCTGAAAGGCTGCAAC-ACC 100
| |||||||||||||||||||||||||||||||||||||||||||||||||||||||||||||||| |||||||||||||||||||||| |
GSTTGAGCCGGGTAGGGAAAGCAGCCTAAAGCCCGGGACAGGCACACAGGCCCAGGTGTGTAGGCCACAGCAGCYGCAGTCCTGAAAGGCTGCAACRYC- 100

CAGACCTCCAGGAGAGACCAGGCCCAGGATGCCTCGCCTGTTCTTGTTCCACCTGCTAGAATTCTGTTTACTACTGAACCAATTTTCCAGAGCAGTCGCG 200
| |||||||||||||||||||||||||||||||||||||||||||| || ||||||||||||| | ||||||||||||||||||||||||||||||||
CMGACCTCCAGGAGAGACCAGGCCCAGGATGCCTCGCCTGTTYTTKTTCCACCTGCTAGRAKTCTGTTTACTACTGAACCAATTTTCCAGAGCAGTCGCG 200

G-C-CAAATGGAAGGACGATGTTATTAAATTATGCGGCCGCGAATTAGTTCGCGCGCAGATTGCCATTTGCGGCATGAGCACCTGGAGCAAAAGGTCTCT 300
| |       ||||| ||| || ||||||||||||||||||||||||||||||||||||||||||||||||||||||||||||||||||||||||||||
GMCWM--ATGGAWGGASGAWGTTATTAAATTATGCGGCCGCGAATTAGTTCGCGCGCAGATTGCCATTTGCGGCATGAGCACCTGGAGCAAAAGGTCTCT 300

GAGCCAGGAAGATGCTCCTCAGACACCTAGACCAGTGGCAGAAATTGTACCATCCTTCATCAACAAAGATACAGAAACTATAATTATCATGTTGGAATTC 400
||||||||||||||||||||||||||||||||||||||||||||||||||||||||||||||||||||||||||||||||||||||||||||||||||
GAGCCAGGAAGATGCTCCTCAGACACCTAGACCAGTGGCAGAAATTGTACCATCCTTCATCAACAAAGATACAGAAACTATAATTATCATGTTGGAATTC 400

ATTGCTAATTTGCCACCGGAGCTGAAGGCAGCCCTATCTGAGAGGCAACCATCATTACCAGAGCTACAGCAGTATGTACCTGCATTAAAGGATTCCAATC 500
||||||||||||||||||||||||||||||||||||||||||||||||||||||||||||||||||||||||||||||||||||||||||||||||||
ATTGCTAATTTGCCACCGGAGCTGAAGGCAGCCCTATCTGAGAGGCAACCATCATTACCAGAGCTACAGCAGTATGTACCTGCATTAAAGGATTCCAATC 500

TTAGCTTTGAAGAATTTAAGAAACTTATTCGCAATAGGCAAAGTGAAGCCGCAGACAGCAATCCTTCAGAATTAAAATACTTAGGCTTGGATACTCATTC 600
||||||||||||||||||||||||||||||||||||||||||||||||||||||||||||||||||||||||||||||||||||||||||||||||||
TTAGCTTTGAAGAATTTAAGAAACTTATTCGCAATAGGCAAAGTGAAGCCGCAGACAGCAATCCTTCAGAATTAAAATACTTAGGCTTGGATACTCATTC 600

TCAAAAAAGAGACGACCCTACGTGGCACTGTTTGAGAAATGTTGCCTAATTGGTTGTACCAAAAGGTCTCTTGCTAAATATTGCTGAGATGAAGCTAAT 700
||||||||||||||||||||||||||||||||||||||||||||||||||||||||||||||||||||||||||||||||||||||||||||||||||
TCAAAAAAGAGACGACCCTACGTGGCACTGTTTGAGAAATGTTGCCTAATTGGTTGTACCAAAAGGTCTCTTGCTAAATATTGCTGAGATGAAGCTAAT 700

TGTGCACATCTTGTCTAATTTTCCACACATAGTCTTGATGACATTTCACTGATGCTTCTGTCAGGTCCCACTAATTATTAGAATATAAGAAATCTTTATT 800
||||||||||||||||||||||||||||||||||||||||||||||||||||||||||||||||||||||||||||||||||||||||||||||||||
TGTGCACATCTTGTCTAATTTTCCACACATAGTCTTGATGACATTTCACTGATGCTTCTGTCAGGTCCCACTAATTATTAGAATATAAGAAATCTTTATT 800

AATGTTTAGATTTTTCATTTGGTGTGTAAGAAAATATTCTTTGTATGATTGTAGTTTCTGTAAATGACACTTTCTATGCTGAAGTCTTTTTGTCTTTTTA 900
||||||||||||||||||||||||||||||||||||||||||||||||||||||||||||||||||||||||||||||||||||||||||||||||||
AATGTTTAGATTTTTCATTTGGTGTGTAAGAAAATATTCTTTGTATGATTGTAGTTTCTGTAAATGACACTTTCTATGCTGAAGTCTTTTTGTCTTTTTA 900

TTAACAGTATAATTGTGTTGATTCTTTTTAATGCTGTTAACTTAAAATTACAATAAAACCTTTGCCACTTTT                              967
||||||||||||||||||||||||||||||||||||||||||||||||||||||||||||||||||||||
TTAACAGTATAATTGTGTTGATTCTTTTTAATGCTGTTAACTTAAAATTACAATAAAACCTTTGCCACTTTT                              967
```

Alignment of RLX 1 sequences from controls (strand a; SEQ ID NO: 1) and subjects with MS (strand B; SEQ ID NO: 2). Multiple mutations appear in the first 210 base pairs as shown.

TABLE 2

Sequence Comparison of RLX1

```
C    MPRLFLFHLLEFCLLLNQFSRAVAAKWKDDVIKLCGRELVRAQIAICGMSTWSKR
MS   MPRLFFFHLLGVCLLLNQFSRAVADSWMEEVIKLCGRELVRAQIAICGMSTWSKR

C    SLSQEDAPQTPRPVAEIVPSFINKDTETIIIMLEFIANLPPELKAALSERQPSLPELQ
MS   SLSQEDAPQTPRPVAEIVPSFINKDTETIIIMLEFIANLPPELKAALSERQPSLPELQ
```

TABLE 2-continued

Sequence Comparison of RLX1

```
C    QYVPALKDSNLSFEEFKKLIRNRQSEAADSNPSELKYLGLDTHSQKKRRPYVALFEK
MS   QYVPALKDSNLSFEEFKKLIRNRQSEAADSNPSELKYLGLDTHSQKKRRPYVALFEK

C    CCLIGCTKRSLAKYC
MS   CCLIGCTKRSLAKYC
```

Protein sequence for RLX 1 showing differences between control (SEQ ID NO: 3) and subjects with MS (SEQ ID NO: 4). The identified changes in sequence of the protein also caused changes in the secondary and tertiary structure of the mature protein. There are a number of protein changes around the β-chain binding cassette which is a conformational and electrostatic binding region.
*Text in bold italics text is the β chain binding cassette sequence.

Figure 1:
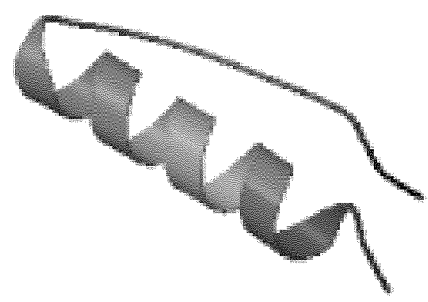
FIG. 1 shows conformational changes in the β chain binding cassette between the wild type relaxin 1 (a) and relaxin 1 from subjects with MS (b). Since the relaxin binding cassette is dependent on conformation and electrostatic forces the changes could influence the ability of RLX 1-MS to bind to its receptor.
Figure 1:
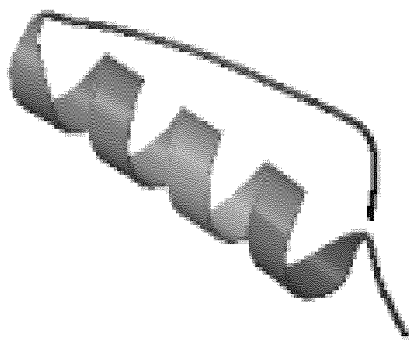
Figure 2:
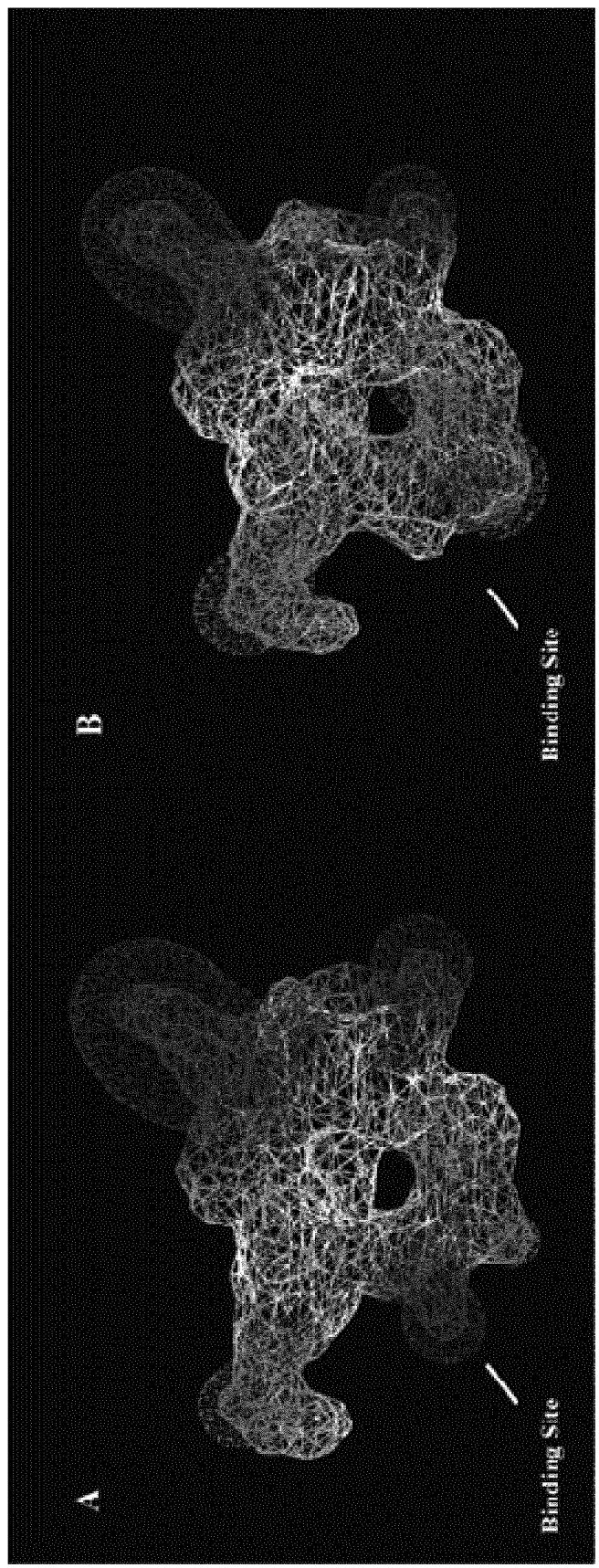
FIG. 2 shows differences in electrostatic charges between wild type relaxin 1 (a) and MS relaxin (b). The changes in electrostatic forces due to amino acid substitution in relaxin 1 from MS subjects will affect its ability to bind its receptor.

The variations in the sequence of RLX1 found in subjects with MS could have an effect of the β chain binding cassette region. The β chain binding cassette has been shown to be controlled by both its geometry and electrostatic forces Protein modeling was performed to determine the effect of amino acids substitutions on the structure and function of the binding site using Swiss Prot. Changes in the Protein's geometry were observed between the wild type and MS. (See FIG. 1). The electrostatic forces associated with the binding site were also greatly altered (See FIG. 2).

The polymorphisms in the gene for relaxin 1 translate into changes of the amino acid sequence of the mature protein. These amino acid changes affect both the geometrical stability of the protein and the electrostatic charges associated with the β chain binding cassette. Both of these are essential for correct binding and functioning of relaxin 1.

The changes in the binding could also affect the levels of relaxin 1 in the sera, mainly due to the fact that relaxin one production is suppressed by a feedback mechanism. This feedback is mediated through the binding of the β chain binding cassette to its receptor. Impaired binding of the β chain cassette would not activate the feedback mechanism and result in an overproduction of relaxin 1.

EXAMPLE 2

Circulating Serum Levels of Relaxin 1 in Multiple Sclerosis

The changes in the B chain binding site of relaxin 1 were investigated to determine whether they affected the circulating levels in subjects with MS.

Sera samples were taken from controls (n=4) and a group of MS patients (n=16). The MS patients included subjects with all three forms of the disease; relapsing remitting (RR), chronic progressive (CP) and secondary progressive (SP). The samples were randomized and assayed blind. Serum relaxin levels were determined by ELISA (Alpco Immunoassays, Salem, N.H.) according to the manufacturer's directions. The raw data was analysed using MasterPlex, Version: 2.0.0.73, Released May 5, 2011. There were significant differences in the sera levels of relaxin between the controls and all three MS groups (see FIG. 3).

Relaxin levels in the control group (Ave.=26.84 pg/ml) were consistent with published levels. Levels of relaxin in both RR and CP MS were significantly elevated (*RR=908.95 pg/ml & CP=87.30 pg/ml). However, there was no detectable relaxin present in the SP patients. The small sample size of SP (n=2) is not statistically significant. It is interesting though since SP MS does not respond to treatment in the same way as RR and CP. This has fostered the idea that SP may have a distinct etiology from RR and CP. The total lack of measurable relaxin the sera of these two SP subjects would support this hypothesis.

Although the average sera relaxin levels in RR and CP were different, the low ranges were similar between the two groups (RR=54.63–2291.63 & CP=46.28–129.09) while the high range differed significantly. The RR subjects with the highest levels of relaxin all reported having an exacerbation within the previous 4 months. Showing a positive correlation between inflammatory events and sera relaxin levels (see Table 3)

TABLE 3

| Sample Number | Disease Type | Sex | Age | Weeks Since Last Exacerbation | Relaxin (pg/ml) |
| --- | --- | --- | --- | --- | --- |
| 1 | Control | F | 51 | — | 25.18 |
| 2 | Control | F | 46 | — | 30.73 |
| 3 | Control | F | 52 | — | 27.66 |
| 4 | Control | M | 36 | — | 23.79 |
| 5 | RR | F | 61 | 4 | 332.56 |
| 6 | RR | F | 65 | 12 | 193.43 |
| 7 | SPMS | F | 64 | — | 0.00 |
| 8 | CP | F | 41 | — | 98.25 |
| 9 | CP | F | 38 | — | 134.4 |
| 10 | CP | M | 65 | — | 129.09 |
| 11 | CP | F | 87 | — | 66.98 |
| 12 | CP | M | 34 | — | 59.9 |
| 13 | CP | M | 58 | — | 46.28 |
| 14 | RR | F | 69 | 24 | 54.63 |
| 15 | RR | M | 64 | 8 | 2156.54 |
| 16 | RR | F | 45 | 7 | 2291.63 |
| 17 | SPMS | F | 37 | — | 0.00 |
| 18 | CP | F | 56 | — | 76.21 |
| 19 | RR | M | 61 | 6 | 68.54 |
| 20 | RR | F | 43 | 15 | 1265.32 |

Relaxin levels in the sera of MS and Controls measured by ELISA. The controls relaxin levels were Ave. 26.84 (mean=26.42), relaxin levels in MS sera were Ave. 435.86 (mean=87.23). There was no correlation between disease type, sex, age or time since last exacerbation.

The results of this study show that levels of sera relaxin are elevated in RR and CP form of MS. With a positive correlation between the level of relaxin and recent inflammatory events. The mutation in the β chain binding cassette of relaxin identified in subjects with RR and CP MS alters the ability of relaxin 1 to bind to its receptor. Thus the feedback loop which controls relaxin production is not activated. Resulting in an over-production of relaxin in response to stress or inflammation. This is consistent with the findings of this study. In contrast to RR and CP MS, in SP MS there was no detectable relaxin present.

From the gene studies relaxin 1 in RR and CP forms of MS lack a functional B chain binding site. This is of particular interest since relaxin 1 & 2β chain binding to their receptors increases IL-10, cAMP, TH-2 and Tyrosine Kinase levels. All of which have been shown to be below normal levels in MS. Tyrosine Kinase is also important in maintaining the integrity of the blood brain barrier (BBB). The loss of integrity in the BBB is a hallmark of MS. Relaxin 3 increases TH-1 and decreases cAMP, TH-2, and tyrosine kinase. Therefore, a lack of relaxin 1 in the presence of relaxin 3 could produce the levels of IL-10, cAMP, TH-1 and Tyrosine Kinase which is seen in MS. It has been hypothesized that relaxins effect of IL-10, CD-4, TH-1 and TH-2 contribute to the homeostasis of the immune system and down-regulate auto-immunity.

The mutations in the β chain binding site of relaxin 1 in MS reported here would support the hypothesis that relaxin 2 binding to the relaxin 1 receptor modulates the symptoms of MS. The presence of relaxin 2 in MS essentially acts as a hormone replacement therapy for the inactive relaxin 1. Therefore, hormone replacement therapy with relaxin 2 could be used to manage the symptoms and inflammatory events in MS.

The use of relaxin 1 or 2 in the treatment of MS is further supported by the ability of both to bind and activate the glucocorticoid receptor. Corticosteroids also bind to the glucocorticoid receptor and down regulate inflammation and modulate the immune system. They are a proven tool in the treatment of MS.

Although corticosteroids provide an effective treatment for MS symptoms they do have severe side effects, especially with long-term usage Some of the mild side affects include: increased appetite; indigestion; nervousness or restlessness; trouble sleeping; headache; increased sweating; unusual increase in hair growth on body or face. Less common side effects are: severe mood changes or mood swings; decreased or blurred vision; frequent urination.

Side effects of long term use of corticosteroids include: acne or other skin problems; swelling of the face; swelling of the feet or lower legs; rapid weight gain; pain in the hips or other joints (caused by bone cell degeneration); bloody or black, tarry stools; elevated blood pressure; markedly increased thirst (with increased urination indicative of diabetes mellitus); menstrual irregularities; unusual bruising of the skin; thin, shiny skin; hair loss; muscle cramps or pain.

In contrast to corticosteroids, treatment with relaxin 1 and 2 have only minor side effects associated with them. These include: nausea; diarrhea; anxiety; breast tenderness; increased menstrual flow; and acne. However, these side effects are transient and disappear 7-10 days after beginning treatment as the body adjusts to the hormone levels. Thus relaxin 1 and/or 2 are ideal candidates for the treatment of MS symptoms, because of their ability to safely replace corticosteroids use and as a hormone replacement therapy. In RR and CP they would replace the non-binding relaxin 1. Or in the case of SP MS to bring the level of relaxin in the sera up to normal. RLX1 & 2 play important roles as regulators of inflammation, autoimmunity, stabilization of the blood brain barrier and as enhancers of remyelination. A decrease in the ability of RLX1 to bind its receptors will result in a decrease in interferon beta production, increased autoimmunity, decreased blood brain barrier stability, increased levels of CAM and reduced receptor agonist activity for the corticosteroid, GPCR17, LGR7 and PPAR-γ receptors. FIG. 6 summarises the relaxin pathways.

TABLE 5

Analogs of Relaxin in the Treatment of Multiple Sclerosis

| Treatment | Mode of Action | Side Effects | Response to Treatment | | Relaxin Activity |
| --- | --- | --- | --- | --- | --- |
| | | | Symptoms | Disease Progression | |
| Prednisone (Corticosteroid) | Binds Corticosteroid Receptor | Sudden Weight Gain, Cataracts, Depression, Glaucoma, Osteoporosis | Stops Acute Exacerbations | — | Binds Corticosteroid Receptor |
| Avonex (interferon beta-1a) | Increase interferon beta-1a levels | Mostly Mild, Rare Severe Side Effects Reported | Decreases Relapse Rate | Slows Disease Progression | Up Regulates Interferon beta Production |
| Rebif (interferon beta-1a) | Increase interferon beta-1a levels | | Decreases Relapse Rate | Slows Disease Progression | |
| Betaseron (interferon beta-1b) | Increase interferon beta-1b levels | | Decreases Relapse Rate | Slows Disease Progression | |
| Extavia (interferon beta-1b) | Increase interferon beta-1b levels | | Decreases Relapse Rate | Slows Disease Progression | |
| Copaxone (glatiramer acetate) | Binds Anti-myelin Antibodies | Transient Side Effects | Decreases Relapse Rate | Slows Progression | Down Regulates Autoimmune Response |
| Novantrone (mitoxantrone) | Immunosuppressant | heart damage and liver dysfunction | Decreases Relapse Rate | Moderate Effects | |
| Tysabri (natalizumab) | Lowers the Level of CAM-1 | Rare cases of leukoencephalopathy reported | Decreases Relapse Rate | Some Effects | Suppresses CAM-1 Expression |
| Gilenya (fingolimod) | S1P; G-coupled Protein Receptor 17 Agonist | Headache, Back Pain Dizziness, Slow Heart Rate, Eye Problems | Decreases Relapse Rate | Some Slowing | G-coupled Protein Receptor 17 Agonist |
| Actos (Pioglitazone) | Peroxisome Proliferator-Activated Receptor γ Agonist | Severe Side Effects | Stops Relapses | Stops Disease Progression | Peroxisome Proliferator-Activated Receptor γ Agonist |

TABLE 4

| | Position | | | | |
|---|---|---|---|---|---|
| | 79,782<br>C<br>AGTGATAGCCCCAT<br>ACTAAAGA | 79,784<br>T<br>TGATAGCCCATAC<br>TAAAGACT | 79,787<br>T<br>TAGCCCATACTAA<br>AGACTGGT | 79,794<br>T<br>TACTAAAGACTGG<br>TTGAGCCG | 79,796<br>G<br>CTAAAGACTGGTT<br>GAGCCGGG |
| NT_008413.103_(RLN1)_Ref | | | | | |
| S900111.MMT-1-RLN1_Contig | C/S | T/W | W | Y | S |
| S900111.MMT-2-RLN1_Contig | C/S | T/W | W | Y | S |
| S900111.MMT-3-RLN1_Contig | C/S | T/W | W | Y | S |
| S900111.MMT-4-RLN1_Contig | C/S | T/W | W | Y | S |
| S900111.MMT-5-RLN1_Contig | C/S | T/W | W | Y | S |
| S900111.MMT-6-RLN1_Contig | C/S | T/W | W | Y | S |
| S900111.MMT-7-RLN1_Contig | C/S | T/W | W | Y | S |
| S900111.MMT-8-RLN1_Contig | C/S | T/W | W | Y | S |
| S900111.MMT-9-RLN1_Contig | C/S | T/W | W | Y | S |
| S900111.MMT-10-RLN1_Contig | C/S | T/W | W | Y | S |
| S900111.MMT-11-RLN1_Contig | C/S | T/W | W | Y | S |
| S900111.MMT-12-RLN1_Contig | C/S | T/W | W | Y | S |
| S900111.MMT-13-RLN1_Contig | C/S | T/W | W | Y | S |
| S900111.MMT-14-RLN1_Contig | C/S | T/W | W | Y | S |
| S900111.MMT-15-RLN1_Contig | C/S | T/W | W | Y | S |
| S900111.MMT-16-RLN1_Contig | C/S | T/W | W | Y | S |
| S900111.MMT-17-RLN1_Contig | C/S | T/W | W | Y | S |
| S900111.MMT-18-RLN1_Contig | C/S | T/W | W | Y | S |
| S900111.MMT-19-RLN1_Contig | C/S | T/W | W | Y | S |
| S900111.MMT-20-RLN1_Contig | C/S | T/W | W | Y | S |
| S900111.MMT-21-RLN1_Contig | C/S | T/W | W | Y | S |
| S900111.MMT-22-RLN1_Contig | C/S | T/W | W | Y | S |
| S900111.MMT-23-RLN1_Contig | C/S | T/W | W | Y | S |
| S900111.MMT-24-RLN1_Contig | C/S | T/W | W | Y | S |

| | Position | | | | |
|---|---|---|---|---|---|
| | 79,869<br>C<br>CCACAGCAGCCCGC<br>AGTCCTGA | 79,891<br>A<br>AGGCTGCAACACC<br>CAGACCTC | 79,892<br>C<br>GGCTGCAACACCC<br>AGACCTCC | 79,895<br>A<br>TGCAACACCCAGA<br>CCTCCAGG | 79,936<br>C<br>CTGCCTGTTCTTG<br>TTCCACC |
| NT_008413.103_(RLN1)_Ref | | | | | |
| S900111.MMT-1-RLN1_Contig | Y | R | Y | M | Y |
| S900111.MMT-2-RLN1_Contig | Y | R | Y | M | Y |
| S900111.MMT-3-RLN1_Contig | Y | R | Y | M | Y |
| S900111.MMT-4-RLN1_Contig | Y | R | Y | M | Y |
| S900111.MMT-5-RLN1_Contig | Y | R | Y | M | Y |
| S900111.MMT-6-RLN1_Contig | Y | R | Y | M | Y |
| S900111.MMT-7-RLN1_Contig | Y | R | Y | M | Y |
| S900111.MMT-8-RLN1_Contig | Y | R | Y | M | Y |
| S900111.MMT-9-RLN1_Contig | Y | R | Y | M | Y |

TABLE 4-continued

| | | | | | |
|---|---|---|---|---|---|
| S900111.MMT-10-RLN1_Contig | Y | R | Y | M | Y |
| S900111.MMT-11-RLN1_Contig | Y | R | Y | M | Y |
| S900111.MMT-12-RLN1_Contig | Y | R | Y | M | Y |
| S900111.MMT-13-RLN1_Contig | Y | R | Y | M | Y |
| S900111.MMT-14-RLN1_Contig | Y | R | Y | M | Y |
| S900111.MMT-15-RLN1_Contig | Y | R | Y | M | Y |
| S900111.MMT-16-RLN1_Contig | Y | R | Y | M | Y |
| S900111.MMT-17-RLN1_Contig | Y | R | Y | M | Y |
| S900111.MMT-18-RLN1_Contig | Y | R | Y | M | Y |
| S900111.MMT-19-RLN1_Contig | Y | R | Y | M | Y |
| S900111.MMT-20-RLN1_Contig | Y | R | Y | M | Y |
| S900111.MMT-21-RLN1_Contig | Y | R | Y | M | Y |
| S900111.MMT-22-RLN1_Contig | Y | R | Y | M | Y |
| S900111.MMT-23-RLN1_Contig | Y | R | Y | M | Y |
| S900111.MMT-24-RLN1_Contig | Y | R | Y | M | Y |

| | Position | | | | |
|---|---|---|---|---|---|
| | 79,939<br>G<br>GCCTGTTCTTGTT<br>CCACCTGC | 79,953<br>A<br>CACCTGCTAGAAT<br>TCTGTTTA | 79,955<br>T<br>CCTGCTAGAATTC<br>TGTTTACT | 79,995<br>C<br>GCAGTCGCGGCCA<br>AATGGAAG | 79,997<br>A<br>AGTCGCGGCCAAA<br>TGGAAGGA |
| NT_008413.103_(RLN1)_Ref | | | | | |
| S900111.MMT-1-RLN1_Contig | K | R | K | M | W |
| S900111.MMT-2-RLN1_Contig | K | R | K | M | W |
| S900111.MMT-3-RLN1_Contig | K | R | K | M | W |
| S900111.MMT-4-RLN1_Contig | K | R | K | M | W |
| S900111.MMT-5-RLN1_Contig | K | R | K | M | W |
| S900111.MMT-6-RLN1_Contig | K | R | K | M | W |
| S900111.MMT-7-RLN1_Contig | K | R | K | M | W |
| S900111.MMT-8-RLN1_Contig | K | R | K | M | W |
| S900111.MMT-9-RLN1_Contig | K | R | K | M | W |
| S900111.MMT-10-RLN1_Contig | K | R | K | M | W |
| S900111.MMT-11-RLN1_Contig | K | R | K | M | W |
| S900111.MMT-12-RLN1_Contig | K | R | K | M | W |
| S900111.MMT-13-RLN1_Contig | K | R | K | M | W |
| S900111.MMT-14-RLN1_Contig | K | R | K | M | W |
| S900111.MMT-15-RLN1_Contig | K | R | K | M | W |
| S900111.MMT-16-RLN1_Contig | K | R | K | M | W |
| S900111.MMT-17-RLN1_Contig | K | R | K | M | W |
| S900111.MMT-18-RLN1_Contig | K | R | K | M | W |
| S900111.MMT-19-RLN1_Contig | K | R | K | M | W |
| S900111.MMT-20-RLN1_Contig | K | R | K | M | W |

TABLE 4-continued

| | | | | | |
|---|---|---|---|---|---|
| S900111.MMT-21-RLN1_Contig | K | R | K | M | W |
| S900111.MMT-22-RLN1_Contig | K | R | K | M | W |
| S900111.MMT-23-RLN1_Contig | K | R | K | M | W |
| S900111.MMT-24-RLN1_Contig | K | R | K | M | W |

| | Position | | | | |
|---|---|---|---|---|---|
| NT_008413.103_(RLN1)_Ref | 79,998<br>A<br>GTCGCGGCCAAAT<br>GGAAGGAC | 80,004<br>A<br>GCCAAATGGAAGG<br>ACGATGTT | 80,008<br>C<br>AATGGAAGGACGA<br>TGTTATTA | 80,011<br>T<br>GGAAGGACGATGT<br>TATTAAAT | Total<br>Differences |
| S900111.MMT-1-RLN1_Contig | M | W | S | W | 19 |
| S900111.MMT-2-RLN1_Contig | M | W | S | W | 19 |
| S900111.MMT-3-RLN1_Contig | M | W | S | W | 19 |
| S900111.MMT-4-RLN1_Contig | M | W | S | W | 19 |
| S900111.MMT-5-RLN1_Contig | M | W | S | W | 19 |
| S900111.MMT-6-RLN1_Contig | M | W | S | W | 19 |
| S900111.MMT-7-RLN1_Contig | M | W | S | W | 19 |
| S900111.MMT-8-RLN1_Contig | M | W | S | W | 19 |
| S900111.MMT-9-RLN1_Contig | M | W | S | W | 19 |
| S900111.MMT-10-RLN1_Contig | M | W | S | W | 19 |
| S900111.MMT-11-RLN1_Contig | M | W | S | W | 19 |
| S900111.MMT-12-RLN1_Contig | M | W | S | W | 19 |
| S900111.MMT-13-RLN1_Contig | M | W | S | W | 19 |
| S900111.MMT-14-RLN1_Contig | M | W | S | W | 19 |
| S900111.MMT-15-RLN1_Contig | M | W | S | W | 19 |
| S900111.MMT-16-RLN1_Contig | M | W | S | W | 19 |
| S900111.MMT-17-RLN1_Contig | M | W | S | W | 19 |
| S900111.MMT-18-RLN1_Contig | M | W | S | W | 19 |
| S900111.MMT-19-RLN1_Contig | M | W | S | W | 19 |
| S900111.MMT-20-RLN1_Contig | M | W | S | W | 19 |
| S900111.MMT-21-RLN1_Contig | M | W | S | W | 19 |
| S900111.MMT-22-RLN1_Contig | M | W | S | W | 19 |
| S900111.MMT-23-RLN1_Contig | M | W | S | W | 19 |
| S900111.MMT-24-RLN1_Contig | M | W | S | W | 19 |

The treatments listed above all target RLX1 receptor mediated pathways. In the absence of active RLX1 these drugs are able to activate some of the receptors and reduce the symptoms of MS. In the presence of functional RLX1 these receptor pathways would all be activated, supporting the use of RLX1 as a treatment for MS.

Further support comes from the discovery that RLX1 is an analog of Actos. Actos (pioglitazone) is a drug developed for diabetes was found to be effective in treating MS. Initial clinical trials have shown that Actos stops relapses, stops disease progression and eliminates inflammation and plaque formation as evidenced by serial MRI.

Actos like the steroids appears to be a very powerful tool in treating MS. Unfortunately, like the steroids and many other treatments, it has side effects. In contrast Relaxin has been shown to have only mild and transient side effects, usually disappearing within 7-10 days.

Furthermore, restoring the natural level of active RLX1 or 2 through RLX hormone replacement therapy could greatly reduce inflammation, down regulate autoimmunity and promote remyelination.

In addition the measurement of relaxin levels in the sera or plasma can be used as an early confirmatory test for MS. This could be used alone or in conjunction with a genetic screen for the mutations of the relaxin 1 gene.

The invention claimed is:

1. A method of treating Multiple Sclerosis which comprises administering to a subject with Multiple Sclerosis a composition, wherein the composition is a pharmaceutical composition which comprises one or more Relaxins optionally together with one or more pharmaceutically acceptable carriers, excipients or diluents, wherein the Relaxins are selected from the group consisting of RLX1, RLX2, and a combination of RLX1 and RLX2.

2. The method according to claim 1, wherein the one or more Relaxins comprises RLX1 or a combination of RLX1 and RLX2.

3. The method according to claim 1, wherein the one or more Relaxins comprises a Prorelaxin of RLX1 or RLX2, or a Preprorelaxin of RLX1 or RLX2, or any combination thereof.

4. The method according to claim 1, wherein the one or more Relaxins consists of RLX2.

5. The method according to claim 1, wherein the one or more Relaxins consists of RLX1.

6. The method according to claim 1, wherein the one or more Relaxins consists of the combination of RLX1 and RLX2.

* * * * *

SEQUENCE LISTING

<160> NUMBER OF SEQ ID NOS: 23

<210> SEQ ID NO 1
<211> LENGTH: 969
<212> TYPE: DNA
<213> ORGANISM: Homo sapiens

<400> SEQUENCE: 1

```
ggttgagccg ggtagggaaa gcagcctaaa gcccgggaca ggcacacagg cccaggtgtg      60
taggccacag cagccgcagt cctgaaaggc tgcaacaccc agacctccag gagagaccag     120
gcccaggatg cctcgcctgt tcttgttcca cctgctagaa ttctgtttac tactgaacca     180
attttccaga gcagtcgcgg ccaaatggaa ggacgatgtt attaaattat gcggccgcga     240
attagttcgc gcgcagattg ccatttgcgg catgagcacc tggagcaaaa ggtctctgag     300
ccaggaagat gctcctcaga cacctagacc agtggcagaa attgtaccat ccttcatcaa     360
caaagataca gaaactataa ttatcatgtt ggaattcatt gctaatttgc caccggagct     420
gaaggcagcc ctatctgaga ggcaaccatc attaccagag ctacagcagt atgtacctgc     480
attaaaggat tccaatctta gctttgaaga atttaagaaa cttattcgca ataggcaaag     540
tgaagccgca gacagcaatc cttcagaatt aaaatactta ggcttggata ctcattctca     600
aaaaaagaga cgaccctacg tggcactgtt tgagaaatgt tgcctaattg ttgtaccaa      660
aaggtctctt gctaaatatt gctgagatga agctaattgt gcacatcttg tctaattttc     720
cacacatagt cttgatgaca tttcactgat gcttctgtca ggtcccacta attattagaa     780
tataagaaat ctttattaat gtttagattt ttcatttggt gtgtaagaaa atattctttg     840
tatgattgta gttctgtaa atgacacttt ctatgctgaa gtcttttttgt cttttttatta    900
acagtataat tgtgttgatt ctttttaatg ctgttaactt aaaattacaa taaaacctt     960
gccactttt                                                              969
```

<210> SEQ ID NO 2
<211> LENGTH: 969
<212> TYPE: DNA
<213> ORGANISM: Homo sapiens

<400> SEQUENCE: 2

```
gsttgagccg ggtagggaaa gcagcctaaa gcccgggaca ggcacacagg cccaggtgtg      60
taggccacag cagcygcagt cctgaaaggc tgcaacrycc mgacctccag gagagaccag     120
gcccaggatg cctcgcctgt tyttkttcca cctgctagra ktctgtttac tactgaacca     180
attttccaga gcagtcgcgg mcwmatggaw ggasgawgtt attaaattat gcggccgcga     240
attagttcgc gcgcagattg ccatttgcgg catgagcacc tggagcaaaa ggtctctgag     300
ccaggaagat gctcctcaga cacctagacc agtggcagaa attgtaccat ccttcatcaa     360
caaagataca gaaactataa ttatcatgtt ggaattcatt gctaatttgc caccggagct     420
gaaggcagcc ctatctgaga ggcaaccatc attaccagag ctacagcagt atgtacctgc     480
attaaaggat tccaatctta gctttgaaga atttaagaaa cttattcgca ataggcaaag     540
tgaagccgca gacagcaatc cttcagaatt aaaatactta ggcttggata ctcattctca     600
aaaaaagaga cgaccctacg tggcactgtt tgagaaatgt tgcctaattg ttgtaccaa      660
aaggtctctt gctaaatatt gctgagatga agctaattgt gcacatcttg tctaattttc     720
cacacatagt cttgatgaca tttcactgat gcttctgtca ggtcccacta attattagaa     780
tataagaaat ctttattaat gtttagattt ttcatttggt gtgtaagaaa atattctttg     840
```

```
tatgattgta gtttctgtaa atgacacttt ctatgctgaa gtcttttgt cttttttatta     900 acagtataat tgtgttgatt ctttttaatg ctgttaactt aaaattacaa taaaaccttt     960
gccactttt                                                             969
```

<210> SEQ ID NO 3
<211> LENGTH: 185
<212> TYPE: PRT
<213> ORGANISM: Homo sapiens

<400> SEQUENCE: 3

```
Met Pro Arg Leu Phe Leu Phe His Leu Leu Glu Phe Cys Leu Leu Leu
1               5                   10                  15

Asn Gln Phe Ser Arg Ala Val Ala Ala Lys Trp Lys Asp Asp Val Ile
            20                  25                  30

Lys Leu Cys Gly Arg Glu Leu Val Arg Ala Gln Ile Ala Ile Cys Gly
        35                  40                  45

Met Ser Thr Trp Ser Lys Arg Ser Leu Ser Gln Glu Asp Ala Pro Gln
    50                  55                  60

Thr Pro Arg Pro Val Ala Glu Ile Val Pro Ser Phe Ile Asn Lys Asp
65                  70                  75                  80

Thr Glu Thr Ile Ile Ile Met Leu Glu Phe Ile Ala Asn Leu Pro Pro
                85                  90                  95

Glu Leu Lys Ala Ala Leu Ser Glu Arg Gln Pro Ser Leu Pro Glu Leu
            100                 105                 110

Gln Gln Tyr Val Pro Ala Leu Lys Asp Ser Asn Leu Ser Phe Glu Glu
        115                 120                 125

Phe Lys Lys Leu Ile Arg Asn Arg Gln Ser Glu Ala Ala Asp Ser Asn
    130                 135                 140

Pro Ser Glu Leu Lys Tyr Leu Gly Leu Asp Thr His Ser Gln Lys Lys
145                 150                 155                 160

Arg Arg Pro Tyr Val Ala Leu Phe Glu Lys Cys Cys Leu Ile Gly Cys
                165                 170                 175

Thr Lys Arg Ser Leu Ala Lys Tyr Cys
            180                 185
```

<210> SEQ ID NO 4
<211> LENGTH: 185
<212> TYPE: PRT
<213> ORGANISM: Homo sapiens

<400> SEQUENCE: 4

```
Met Pro Arg Leu Phe Phe Phe His Leu Leu Gly Val Cys Leu Leu Leu
1               5                   10                  15

Asn Gln Phe Ser Arg Ala Val Ala Asp Ser Trp Met Glu Glu Val Ile
            20                  25                  30

Lys Leu Cys Gly Arg Glu Leu Val Arg Ala Gln Ile Ala Ile Cys Gly
        35                  40                  45

Met Ser Thr Trp Ser Lys Arg Ser Leu Ser Gln Glu Asp Ala Pro Gln
    50                  55                  60

Thr Pro Arg Pro Val Ala Glu Ile Val Pro Ser Phe Ile Asn Lys Asp
65                  70                  75                  80

Thr Glu Thr Ile Ile Ile Met Leu Glu Phe Ile Ala Asn Leu Pro Pro
                85                  90                  95

Glu Leu Lys Ala Ala Leu Ser Glu Arg Gln Pro Ser Leu Pro Glu Leu
            100                 105                 110
```

Gln Gln Tyr Val Pro Ala Leu Lys Asp Ser Asn Leu Ser Phe Glu Glu
            115                 120                 125

Phe Lys Lys Leu Ile Arg Asn Arg Gln Ser Glu Ala Ala Asp Ser Asn
        130                 135                 140

Pro Ser Glu Leu Lys Tyr Leu Gly Leu Asp Thr His Ser Gln Lys Lys
145                 150                 155                 160

Arg Arg Pro Tyr Val Ala Leu Phe Glu Lys Cys Cys Leu Ile Gly Cys
                165                 170                 175

Thr Lys Arg Ser Leu Ala Lys Tyr Cys
            180                 185

<210> SEQ ID NO 5
<211> LENGTH: 21
<212> TYPE: DNA
<213> ORGANISM: Homo sapiens
<220> FEATURE:
<221> NAME/KEY: variation
<222> LOCATION: (11)..(11)
<223> OTHER INFORMATION: c or s

<400> SEQUENCE: 5
agtgatagcc satactaaag a                                         21

<210> SEQ ID NO 6
<211> LENGTH: 21
<212> TYPE: DNA
<213> ORGANISM: Homo sapiens
<220> FEATURE:
<221> NAME/KEY: variation
<222> LOCATION: (11)..(11)
<223> OTHER INFORMATION: t or w

<400> SEQUENCE: 6
tgatagccca wactaaagac t                                         21

<210> SEQ ID NO 7
<211> LENGTH: 21
<212> TYPE: DNA
<213> ORGANISM: Homo sapiens
<220> FEATURE:
<221> NAME/KEY: variation
<222> LOCATION: (11)..(11)
<223> OTHER INFORMATION: t or w

<400> SEQUENCE: 7
tagcccatac waaagactgg t                                         21

<210> SEQ ID NO 8
<211> LENGTH: 21
<212> TYPE: DNA
<213> ORGANISM: Homo sapiens
<220> FEATURE:
<221> NAME/KEY: variation
<222> LOCATION: (11)..(11)
<223> OTHER INFORMATION: t or y

<400> SEQUENCE: 8
tactaaagac yggttgagcc g                                         21

<210> SEQ ID NO 9
<211> LENGTH: 21
<212> TYPE: DNA
<213> ORGANISM: Homo sapiens
<220> FEATURE:
<221> NAME/KEY: variation

```
<222> LOCATION: (11)..(11)
<223> OTHER INFORMATION: g or s

<400> SEQUENCE: 9
ctaaagactg sttgagccgg g                                              21

<210> SEQ ID NO 10
<211> LENGTH: 21
<212> TYPE: DNA
<213> ORGANISM: Homo sapiens
<220> FEATURE:
<221> NAME/KEY: variation
<222> LOCATION: (11)..(11)
<223> OTHER INFORMATION: c or y

<400> SEQUENCE: 10
ccacagcagc ygcagtcctg a                                              21

<210> SEQ ID NO 11
<211> LENGTH: 21
<212> TYPE: DNA
<213> ORGANISM: Homo sapiens
<220> FEATURE:
<221> NAME/KEY: variation
<222> LOCATION: (11)..(11)
<223> OTHER INFORMATION: a or r

<400> SEQUENCE: 11
aggctgcaac rcccagacct c                                              21

<210> SEQ ID NO 12
<211> LENGTH: 21
<212> TYPE: DNA
<213> ORGANISM: Homo sapiens
<220> FEATURE:
<221> NAME/KEY: variation
<222> LOCATION: (11)..(11)
<223> OTHER INFORMATION: c or y

<400> SEQUENCE: 12
ggctgcaaca yccagacctc c                                              21

<210> SEQ ID NO 13
<211> LENGTH: 21
<212> TYPE: DNA
<213> ORGANISM: Homo sapiens
<220> FEATURE:
<221> NAME/KEY: variation
<222> LOCATION: (11)..(11)
<223> OTHER INFORMATION: a or m

<400> SEQUENCE: 13
tgcaacaccc mgacctccag g                                              21

<210> SEQ ID NO 14
<211> LENGTH: 21
<212> TYPE: DNA
<213> ORGANISM: Homo sapiens
<220> FEATURE:
<221> NAME/KEY: variation
<222> LOCATION: (11)..(11)
<223> OTHER INFORMATION: c or y

<400> SEQUENCE: 14
ctcgcctgtt yttgttccac c                                              21

<210> SEQ ID NO 15
```

-continued

```
<211> LENGTH: 21
<212> TYPE: DNA
<213> ORGANISM: Homo sapiens
<220> FEATURE:
<221> NAME/KEY: variation
<222> LOCATION: (11)..(11)
<223> OTHER INFORMATION: g or k

<400> SEQUENCE: 15
gcctgttctt kttccacctg c                                              21

<210> SEQ ID NO 16
<211> LENGTH: 21
<212> TYPE: DNA
<213> ORGANISM: Homo sapiens
<220> FEATURE:
<221> NAME/KEY: variation
<222> LOCATION: (11)..(11)
<223> OTHER INFORMATION: a or r

<400> SEQUENCE: 16
cacctgctag rattctgttt a                                              21

<210> SEQ ID NO 17
<211> LENGTH: 21
<212> TYPE: DNA
<213> ORGANISM: Homo sapiens
<220> FEATURE:
<221> NAME/KEY: variation
<222> LOCATION: (11)..(11)
<223> OTHER INFORMATION: t or k

<400> SEQUENCE: 17
cctgctagaa ktctgtttac t                                              21

<210> SEQ ID NO 18
<211> LENGTH: 21
<212> TYPE: DNA
<213> ORGANISM: Homo sapiens
<220> FEATURE:
<221> NAME/KEY: variation
<222> LOCATION: (11)..(11)
<223> OTHER INFORMATION: c or m

<400> SEQUENCE: 18
gcagtcgcgg mcaaatggaa g                                              21

<210> SEQ ID NO 19
<211> LENGTH: 21
<212> TYPE: DNA
<213> ORGANISM: Homo sapiens
<220> FEATURE:
<221> NAME/KEY: variation
<222> LOCATION: (11)..(11)
<223> OTHER INFORMATION: a or w

<400> SEQUENCE: 19
agtcgcggcc waatggaagg a                                              21

<210> SEQ ID NO 20
<211> LENGTH: 21
<212> TYPE: DNA
<213> ORGANISM: Homo sapiens
<220> FEATURE:
<221> NAME/KEY: variation
<222> LOCATION: (11)..(11)
<223> OTHER INFORMATION: a or m

<400> SEQUENCE: 20
```

```
gtcgcggcca matggaagga c                                              21

<210> SEQ ID NO 21
<211> LENGTH: 21
<212> TYPE: DNA
<213> ORGANISM: Homo sapiens
<220> FEATURE:
<221> NAME/KEY: variation
<222> LOCATION: (11)..(11)
<223> OTHER INFORMATION: a or w

<400> SEQUENCE: 21
gccaaatgga wggacgatgt t                                              21

<210> SEQ ID NO 22
<211> LENGTH: 21
<212> TYPE: DNA
<213> ORGANISM: Homo sapiens
<220> FEATURE:
<221> NAME/KEY: variation
<222> LOCATION: (11)..(11)
<223> OTHER INFORMATION: c or s

<400> SEQUENCE: 22
aatggaagga sgatgttatt a                                              21

<210> SEQ ID NO 23
<211> LENGTH: 21
<212> TYPE: DNA
<213> ORGANISM: Homo sapiens
<220> FEATURE:
<221> NAME/KEY: variation
<222> LOCATION: (11)..(11)
<223> OTHER INFORMATION: t or w

<400> SEQUENCE: 23
ggaaggacga wgttattaaa t                                              21
```